(12) United States Patent
Ghoniem

(10) Patent No.: US 9,339,329 B2
(45) Date of Patent: May 17, 2016

(54) BLADDER DENERVATION FOR TREATING OVERACTIVE BLADDER

(71) Applicant: The Regents of the University of California, Oakland, CA (US)

(72) Inventor: Gamal Ghoniem, Aliso Viejo, CA (US)

(73) Assignee: The Regents of the University of California, Oakland, CA (US)

( * ) Notice: Subject to any disclaimer, the term of this patent is extended or adjusted under 35 U.S.C. 154(b) by 72 days.

(21) Appl. No.: 14/029,467

(22) Filed: Sep. 17, 2013

(65) Prior Publication Data

US 2014/0081257 A1 Mar. 20, 2014

Related U.S. Application Data

(60) Provisional application No. 61/702,176, filed on Sep. 17, 2012.

(51) Int. Cl.
| | | |
|---|---|---|
| *A61B 18/12* | (2006.01) |
| *A61B 18/14* | (2006.01) |
| *A61B 18/18* | (2006.01) |
| *A61B 19/00* | (2006.01) |
| *A61B 18/00* | (2006.01) |

(52) U.S. Cl.
CPC ............ *A61B 18/1485* (2013.01); *A61B 18/18* (2013.01); *A61B 18/1477* (2013.01); *A61B 19/54* (2013.01); *A61B 2018/00434* (2013.01); *A61B 2018/00517* (2013.01); *A61B 2018/00523* (2013.01); *A61B 2018/143* (2013.01); *A61B 2018/1425* (2013.01); *A61B 2018/1427* (2013.01); *A61B 2018/1432* (2013.01); *A61B 2018/1475* (2013.01)

(58) Field of Classification Search
CPC ........... A61B 18/1477; A61B 18/1485; A61B 18/18; A61B 2018/00434; A61B 2018/00517; A61B 2018/00523; A61B 2018/1425; A61B 2018/1427; A61B 2018/143; A61B 2018/1432; A61B 2018/1475
See application file for complete search history.

(56) References Cited

U.S. PATENT DOCUMENTS

| | | | | |
|---|---|---|---|---|
| 4,998,930 | A | | 3/1991 | Lundahl |
| 5,385,577 | A | * | 1/1995 | Maurer et al. .................. 607/41 |
| 5,827,276 | A | * | 10/1998 | LeVeen et al. .................. 606/41 |
| 6,235,877 | B1 | | 5/2001 | Scolastico et al. |
| 6,292,695 | B1 | | 9/2001 | Webster, Jr. et al. |

(Continued)

OTHER PUBLICATIONS

Westney, O.L., et al., Long-term results of Ingelman-Sundberg denervation procedure for urge incontinence refractory to medical therapy, J. Urol. Sep. (2002);168(3): 1044-7.

*Primary Examiner* — Michael Peffley
*Assistant Examiner* — Daniel Fowler
(74) *Attorney, Agent, or Firm* — Berliner Steffin Azod LLP

(57) ABSTRACT

A device and method for transvaginal or transrectal treatment of a bladder pathology. The device includes an elongate body that includes a longitudinal axis, a handle at one end of the body, a head at the other end of the body, and a shaft between the handle and the head. The head includes a substantially flat surface and one or more retractable needle electrodes extending through the flat surface. The method includes inserting a probe into a vagina or rectum of a patient, where the probe includes a head portion comprising one or more retractable needle electrodes; heating one or more pelvic nerves supplying the patient's bladder by emitting radiofrequency energy from the one or more needle electrodes; and as a result of the heating, damaging the one or more pelvic nerves.

9 Claims, 7 Drawing Sheets

(56) References Cited

U.S. PATENT DOCUMENTS

| | | | |
|---|---|---|---|
| 6,463,331 B1 * | 10/2002 | Edwards | 607/101 |
| 6,692,490 B1 | 2/2004 | Edwards | |
| 2003/0069620 A1 | 4/2003 | Li | |
| 2003/0130575 A1 * | 7/2003 | Desai | 600/417 |
| 2013/0066308 A1 | 3/2013 | Landman | |

\* cited by examiner

BLADDER DENERVATION FOR TREATING OVERACTIVE BLADDER

BACKGROUND

1. Field of the Invention

The invention relates to an apparatus and treatment for bladder pathologies.

2. Related Art

Urinary bladder pathology results from overactivity of the detrussor (bladder wall) musculature. Bladder pathology, including problems of bladder overactivity and possibly interstitial cystitis, are also thought to result from overactivity or improper activity of the innervations of the bladder.

Problems of bladder overactivity are typically resolved using medications to pharmacologically reduce over activity of the bladder's nerves. These medications, including anticholinergic medications, are used by a very large population of patients. The medications are effective in most, but not all cases. Additionally, the medications have significant systemic side effects and the majority of patients stop taking it by one year (decreased patient compliance). This could be reduced by a localized treatment strategy. Surgical denervation using the Ingelman-Sundberg procedure have also been used to treat urge incontinence.

SUMMARY

In one aspect, a device for transvaginal or transrectal treatment of a bladder pathology is provided. The device includes an elongate body that includes a longitudinal axis, a handle at one end of the body, a head at the other end of the body, and a shaft between the handle and the head. The head includes a substantially flat surface and one or more retractable needle electrodes extending through the flat surface. The shaft and the head are sized and configured to be received in a patient's vagina or rectum.

In the device, the head can contain an array of needle electrodes arranged in rows transverse to the longitudinal axis, and in some embodiments, the rows can be spaced about 1 cm apart. The one or more needle electrodes in some embodiments are curved. The flat surface of the device can be about 3 mm in length in a direction parallel to the longitudinal axis, and/or can be from about 1 to about 2 cm in width in a direction transverse to the longitudinal axis.

In some embodiments, the shaft includes one or more markers for guiding depth of insertion into the patient. In some embodiments, the handle includes controls for turning the device off and on and for regulating radiofrequency energy levels, and/or a slider for extending and retracting the needle electrodes.

In another aspect, a method is provided for treating a bladder pathology involving pelvic nerves. The method includes: inserting a probe into a vagina or rectum of a patient, where the probe includes a head portion comprising one or more retractable needle electrodes; heating one or more pelvic nerves supplying the patient's bladder by emitting radiofrequency energy from the one or more needle electrodes; and as a result of the heating, damaging the one or more pelvic nerves. The head portion of the probe can include a substantially flat surface through which the one or more retractable needle electrodes extend.

In the method, the damaging can include causing a heat lesion in the one or more pelvic nerves, and/or destroying the one or more pelvic nerves. In some embodiments, the damaging results in bladder denervation, and/or the damaging reduces overactivity of the bladder.

In the method, the bladder pathology can involve urinary frequency, urinary urgency, and urge incontinence, overactive bladder, painful bladder syndrome, interstitial cystitis, chronic pelvic pain, pelvic pain because of levator ani trigger points, levator ani and puborectalis spasm, constipation, levator muscle spasm, pelvic floor trigger point, pelvic pain, constipation secondary to puborectalis muscle spasm, anal pain and proctitis, or symptoms of chronic prostatitis without infection. In some embodiments, the bladder pathology is overactive bladder.

The radiofrequency energy can be applied to a central location proximal to the level of the patient's trigone, and can be applied to a location 30 degrees from the midline to either side of the central location.

BRIEF DESCRIPTION OF THE DRAWINGS

For a more complete understanding of the present invention, reference is now made to the following descriptions taken in conjunction with the accompanying drawings, in which:

FIG. 4A is a top plan view, FIG. 4B is a side view, and FIG. 4C is a front view from the head toward the handle.

FIG. 5A is a perspective view of the device, FIG. 5B is perspective view of the head and shaft, and FIG. 5C is a perspective view of the handle.

DETAILED DESCRIPTION

The following is incorporated by reference herein: Provisional Patent Application No. 61/702,176, filed on Sep. 17, 2012.

Figure 1:
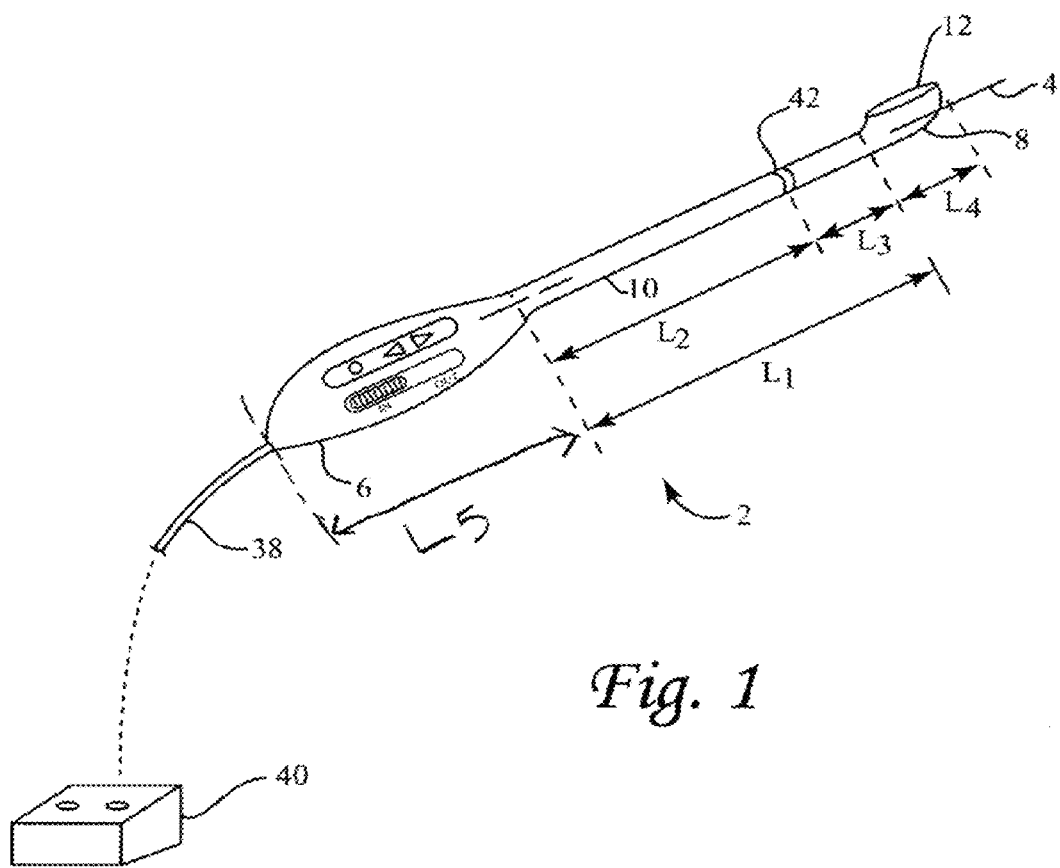
FIG. 1 is drawing of a device for treating bladder pathologies.

Referring to FIG. 1 showing an embodiment of the device, the device includes an elongate body 2 that includes a longitudinal axis 4, a handle 6 at one end of the body, a head 8 at the other end of the body, and a shaft 10 between the handle and the head. The head includes a substantially flat surface 12 and an array of retractable needle electrodes (shown retracted) that can extend and project through the flat surface. In FIG. 1, the term $L_1$ refers to the length of the shaft, while the terms $L_2$ and $L_3$ refer to lengths of shaft subsections, with $L_2+L_3=L_1$. The term $L_4$ refers to the length of the head. The term $L_5$ refers to the length of the handle. In general, the shaft and head are sized and configured to be received in a patient's vagina or rectum. In some embodiments, $L_1$ can be 10 cm-20 cm. In some embodiments, $L_5$ can be 9 cm-12 cm. In a particular embodiment, $L_1$ is about 15 cm, $L_2$ is about 10 cm and $L_3$ is about 5 cm, and $L_4$ is about 4 cm.

Figure 2A:
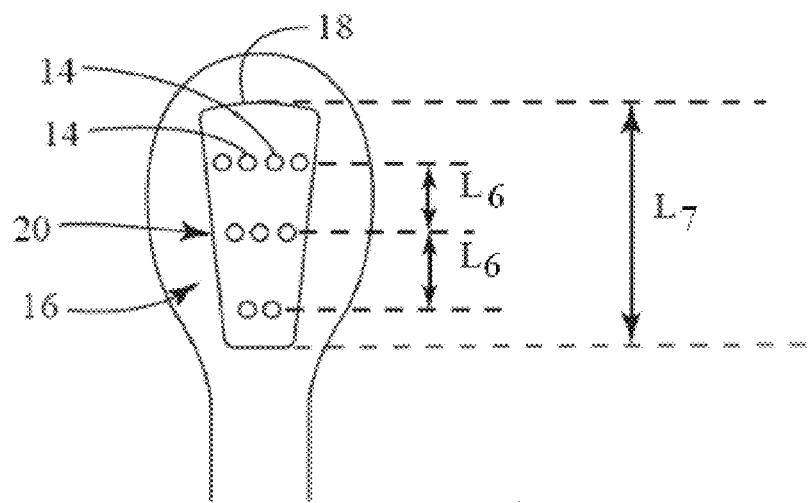
FIG. 2A is a top plan view of a head for a bladder treatment device.
Figure 2B:
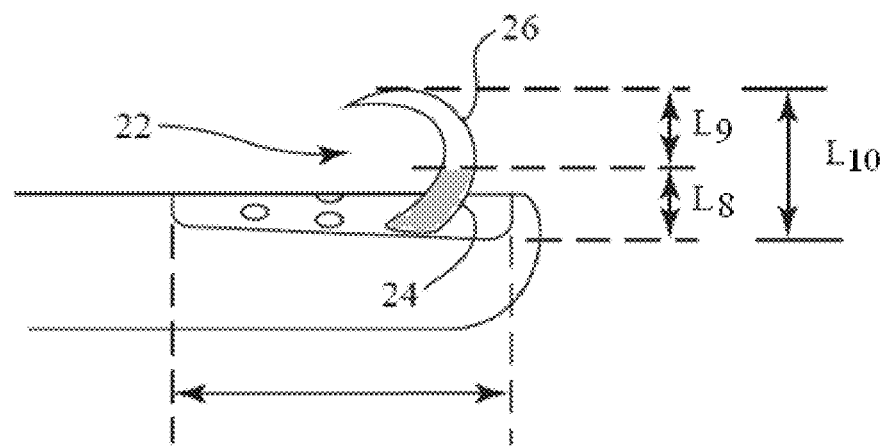
FIG. 2B is a side view of a head for a bladder treatment device.

Positions 14 of retractable needle electrodes forming a needle electrode array 16 on a flat surface 18 of the head are shown in the embodiment in FIG. 2A. The number of needle electrodes can vary depending on the size of the body portion to be exposed to radiofrequency energy. The needle electrodes can be arranged in rows 20 that run transverse to the longitudinal axis of the elongate body. In the figure, the term $L_6$ refers to the spacing between rows, and can be 0.5 cm-1.5 cm. In particular embodiments, $L_6$ can be about: 0.5 cm, about 1 cm, or about 1.5 cm. The term $L_7$ refers to the length of the flat surface in a direction parallel to the longitudinal axis of the device. The width of the flat surface can be measured in a direction transverse to the longitudinal axis of the device. The length and width can vary according to the size and configuration of the head and the number of needle electrodes. $L_7$ can be 2 cm-5 cm, and in particular embodiments is about: 2 cm, 3 cm, 4 cm, or 5 cm. The width of the flat surface can range from about 1 to about 4 cm, and in some embodiments is about: 1 cm, 2 cm, 3 cm, or 4 cm. In the embodiment in FIG. 2B, an example of a curved needle electrode 22 is shown projecting through the flat surface of the head. In this example, the base 24 of the needle electrode is covered with insulation while the tip portion 26 of the needle electrode is not insulated. The distance the base of a needle electrode can extend above the flat surface of the head is referred to as $L_8$ in FIG. 2B, the distance the non-insulated tip portion can extend above the insulated base is referred to as $L_9$, and the total distance the needle electrode can extend above the flat surface is referred to as $L_{10}$, where $L_8+L_9=L_{10}$. $L_8$ can be 1 mm-2 mm, and in particular embodiments is about: 1 mm, 1.5 mm, or 2 mm. $L_9$ can be 2 mm-8 mm, and in particular embodiments is about: 2 mm, 3 mm, 4 mm, 5 mm, 6 mm, 7 mm, or 8 mm. In particular embodiments, $L_8$ is about 2 mm, $L_9$ is about 3 mm, and $L_{10}$ is about 5 mm.

In some embodiments, the overall length of the portion of the needle electrode extending through the flat surface can be between 1-10 mm, and in particular embodiments can be about: 4 mm, or 5 mm.

Figure 3A:
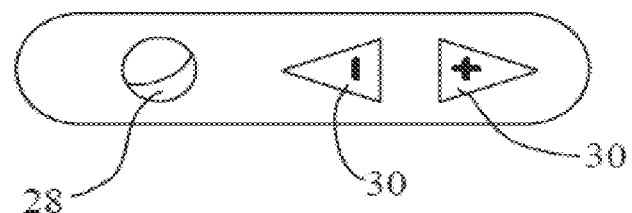
FIGS. 3A and 3B are drawings of various features of a handle for a bladder treatment device.
Figure 3B:
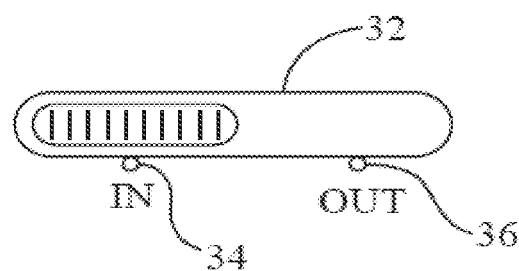

The handle can include one or more controls, buttons, sliders, or switches, or a combination thereof, for controlling and using the device. Such features can be included, for example, for turning the device on and off, for controlling the level of radiofrequency energy emitted, or for controlling the length of the needles electrodes projecting out of the flat surface. In the various embodiments shown in FIGS. 3A and 3B, the handle includes an on-off button 28, radiofrequency power controls 30, and a slider 32 on the side of the handle to control needle electrode extension, having an in 34 and an out 36 position. Referring to FIG. 1, the handle of the device can include a wire 38 for connecting the needle electrodes to a radiofrequency generator 40. The radiofrequency generator can be battery operated and/or rechargeable, and can include a temperature monitoring feature. In addition, the shaft can include one or more markers 42 such as a pattern or guide for guiding the depth of insertion of the device into the patient. A marker can be positioned at length $L_3$ on the shaft of the handle.

Embodiments of the device can thus include the following: an elongate body, a longitudinal axis, a handle at one end of the body, a head at the other end of the body, a shaft between the handle and the head, and an array of retractable needle electrodes on a flat surface of the head.

The device and method for treating bladder pathologies can be used to treat women or men who have urinary frequency, urgency, and urge incontinence. Other indications for the device and method are overactive bladder, painful bladder syndrome, interstitial cystitis, chronic pelvic pain, pelvic pain because of levator ani trigger points, levator ani and puborectalis spasm, constipation, levator muscle spasm, pelvic floor trigger point, pelvic pain, constipation secondary to puborectalis muscle spasm, anal pain and proctitis, or symptoms of chronic prostatitis without infection.

In particular embodiments, a vaginal probe is inserted into a patient and the needle electrodes emit radiofrequency energy, which then destroys the nerves with heat. In one embodiment, a thin wire (probe) is passed through one or more of the needles. In another embodiment, heat treatment causes a heat lesion to the pelvic nerve(s).

In some embodiments, the device is applied subtrigonal and lateral to the trigone in female subjects. In other embodiments, regardless of the subject's sex, the device can be applied to the painful pelvic floor muscle (as in trigger points or spasm). It can be useful in relieving constipation due to puborectalis muscle spasm. In another embodiment, the device is applied transrectally in male subjects. The device can be applied above the prostate for overactive bladder, and to the prostate for chronic prostatitis symptoms without infection.

The radiofrequency energy emitted by the device or by the needle electrodes can be sufficient to heat the tissue to about 65-80° C.; and/or can be capable of generating between 5-10 watts of power.

The device can be applied to a patient for about 30-90 seconds, and between 1-4 ablations can be applied per site.

In some embodiments, the device and method comprise a vaginal probe to deliver radiofrequency waves (RF) through the vaginal wall and posterior to the bladder, where there is dense innervation, to denervate the pelvic nerve(s) supply to the overactive bladder (OAB). OAB is a common condition in the adult (16%) and increases with age.

Some of the advantages of the method and device over previous methods include:
   One time treatment rather than medication every day. In some cases, return of symptoms may be observed due to nerve regeneration. From other denervation surgical procedures, this can happen after a year or more. A subsequent radiofrequency session can then be undertaken.
   Will likely have no systemic side effects.
   Long-term (likely more than 6 months), a single treatment will be cost effective as medication will not be required.
   Will potentially be single outpatient treatment solution for bladder overactivity, interstitial cystitis, and other forms of bladder pathology.

Figure 4A:
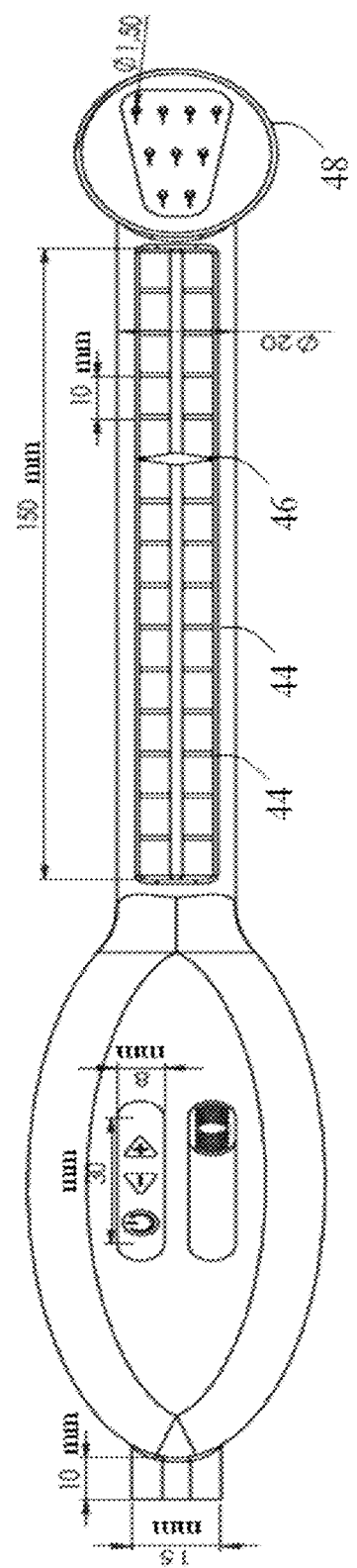
FIGS. 4A-4C are schematic drawings of an embodiment.
Figure 4B:
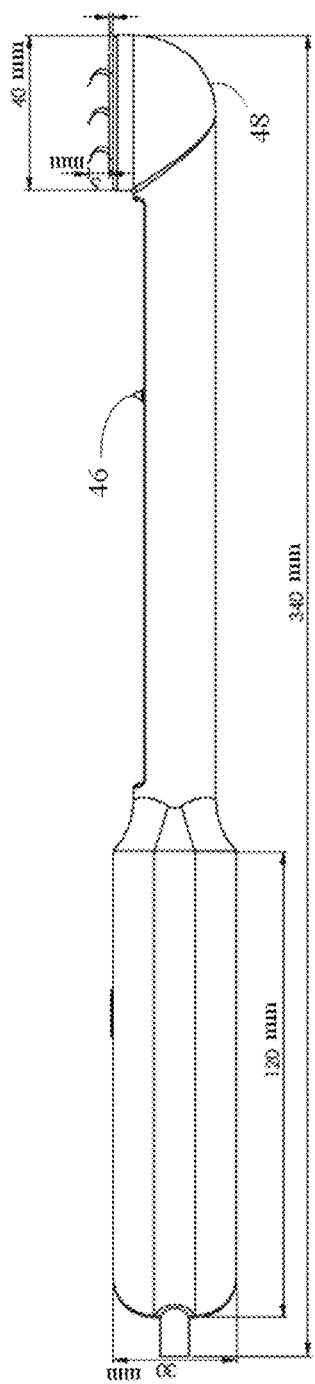
Figure 4C:
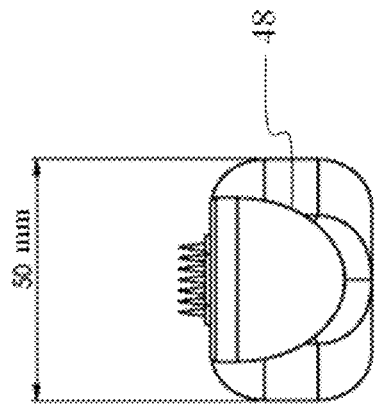
Figure 5A:
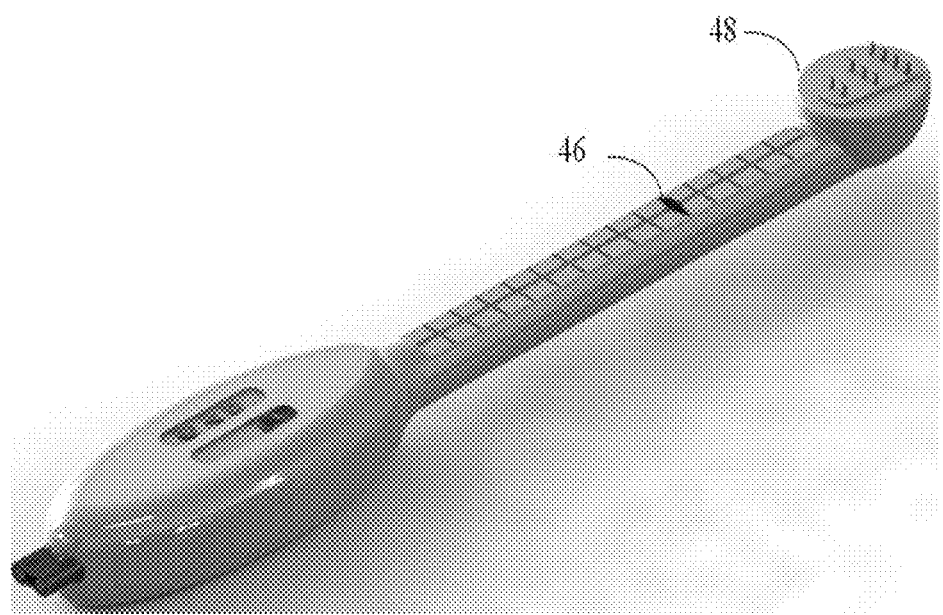
FIGS. 5A-5C are 3D drawings of an embodiment.
Figure 5B:
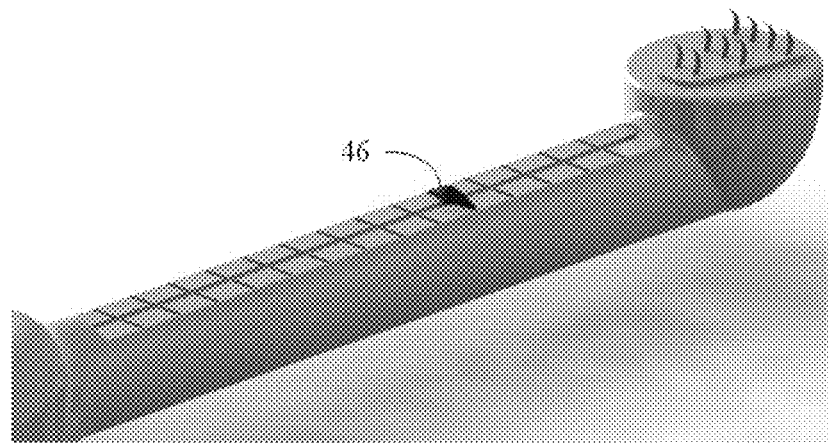
Figure 5C:
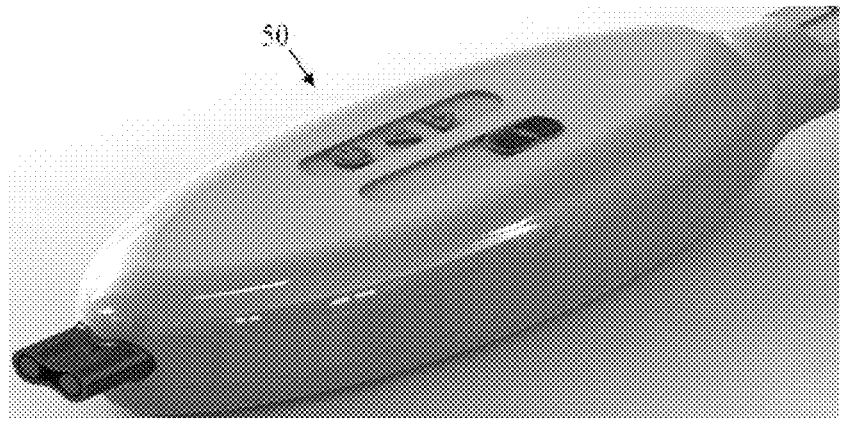

A particular embodiment (called DENERA) is shown in FIGS. 4A-4C. In this embodiments, marker guides 44 provide guides for depth of insertion. Also shown is a protruding guide 46. This embodiment has a 9-electrode head 48. In FIGS. 5A-5C, a 3D drawing of the DENERA device is shown, containing a protruding guide 46 and a 9-electrode head 48. FIG. 5C is a close-up view of a handle 50.

The present invention may be better understood by referring to the accompanying examples, which are intended for illustration purposes only and should not in any sense be construed as limiting the scope of the invention.

EXAMPLE 1

The device can be used by a method involving one or more of the following steps:
   position the patient in lithotomy position,
   prepare vagina lightly with an antiseptic such as Betadine,
   apply local anaesthetic (i.e. cream or jelly) to the area proximal to level of the trigone (about 4 cm from external urethral meatus),
   introduce the device to the position of a "marker",
   once in position, apply mild pressure using index finger behind the head of the device to ensure close contact between the device and patient's tissues,
   deploy the needles on the device,
   turn RF signal on and adjust RF signal if desired using controls, keep RF signal on for 30-90 seconds, off for 30-90 seconds for a total of about 2 to 5 minutes in each site.

apply three times, once to the center (i.e. area proximal to level of the trigone), once 30 degrees to the left of center; and once 30 degrees right of center.

The area treated can be cooled using an ice pack, liquid or other means known in the art. The total procedure may take about 30 minutes.

In some cases, cooling may be applied to the area while the device is on, or after treatment.

REFERENCES

The following publications are incorporated by reference herein.
1. Westney, O. L., et al., Long-term results of Ingelman-Sundberg denervation procedure for urge incontinence refractory to medical therapy, J. Urol. (2002) September; 168(3): 1044-7.
2. U.S. Pat. No. 6,292,695

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A method of treating a bladder pathology involving pelvic nerves, comprising
    inserting a probe having a longitudinal axis into a vagina or rectum of a patient, said probe comprising a head portion that has a flat face that is substantially parallel to the longitudinal axis and comprising an array of retractable needle electrodes that extend from the face substantially perpendicularly to the face,
    heating one or more pelvic nerves supplying the patient's bladder by emitting radiofrequency energy from the array of needle electrodes, and
    as a result of the heating, destroying or causing a heat lesion in the one or more pelvic nerves.

2. The method of claim 1, wherein the heating comprises causing a heat lesion in the one or more pelvic nerves.

3. The method of claim 1, wherein the heating comprises destroying the one or more pelvic nerves.

4. The method of claim 1, wherein the heating results in bladder denervation.

5. The method of claim 1, wherein the heating reduces overactivity of the bladder.

6. The method of claim 1, wherein the bladder pathology involves urinary frequency, urinary urgency, urge incontinence, overactive bladder, painful bladder syndrome, interstitial cystitis, chronic pelvic pain, pelvic pain because of levator ani trigger points, levator ani spasm, puborectalis spasm, constipation, levator muscle spasm, pelvic floor trigger point, pelvic pain, constipation secondary to puborectalis muscle spasm, anal pain, proctitis, or symptoms of chronic prostatitis without infection.

7. The method of claim 6, wherein the bladder pathology is overactive bladder.

8. The method of claim 1, wherein, the radiofrequency energy is applied to a central location proximal to the level of the patient's trigone.

9. The method of claim 8, wherein the radiofrequency energy is further applied to a location 30 degrees to either side of the central location.

\* \* \* \* \*